United States Patent [19]

Tanaka et al.

[11] Patent Number: 5,424,478

[45] Date of Patent: Jun. 13, 1995

[54] PROCESS FOR PRODUCING VITAMIN A DERIVATIVES

[75] Inventors: Mitsutaka Tanaka, Sanda; Tadashi Hanaoka, Toyonaka; Kunio Takanohashi, Kawanishi, all of Japan

[73] Assignee: Takeda Chemical Industries, Ltd., Osaka, Japan

[21] Appl. No.: 215,813

[22] Filed: Mar. 22, 1994

[30] Foreign Application Priority Data

Mar. 23, 1993 [JP] Japan .................................. 5-064031

[51] Int. Cl.⁶ ............................................. C07C 69/07
[52] U.S. Cl. .................................. 560/260; 560/259; 560/128; 562/510; 558/87; 558/88; 558/217; 585/351
[58] Field of Search ..................... 560/128, 259, 260; 562/510; 585/351; 558/217, 87, 88

[56] References Cited

U.S. PATENT DOCUMENTS

| | | | |
|---|---|---|---|
| 4,026,778 | 5/1977 | Lalonde et al. | 204/157.67 |
| 4,175,205 | 11/1979 | Decor | 560/260 |
| 4,916,250 | 4/1990 | Babler | 558/217 |
| 5,043,356 | 8/1991 | Fulton, Jr. | 514/549 |
| 5,112,598 | 5/1992 | Biesalski | 424/46 |
| 5,185,372 | 2/1993 | Ushio et al. | 514/552 |

OTHER PUBLICATIONS

Pommer et al., Pure Appl. Chem., 43, pp. 527–551 (1975).

*Primary Examiner*—Arthur C. Prescott
*Attorney, Agent, or Firm*—Wenderoth, Lind & Ponack

[57] ABSTRACT

The present specification relates to an industrially advantageous process for producing vitamin A derivatives which are useful as medicaments, feed additives, food additives and the like. The process provides vitamin A derivatives, particularly all-trans vitamin A derivatives in high yield and purity.

22 Claims, No Drawings

PROCESS FOR PRODUCING VITAMIN A DERIVATIVES

FIELD OF THE INVENTION

The present invention relates to a process for producing vitamin A derivatives.

BACKGROUND OF THE INVENTION

Vitamin A is a known compound represented by the formula:

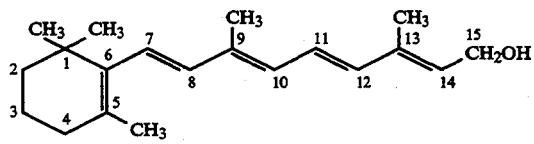

Carboxylic acid ester derivatives such as acetates or palmitates of vitamin A have widely been used as medicaments, food additives, feed additives and the like. These vitamin A derivatives have been produced by various methods.

These methods include the following two processes for producing vitamin A which involve the Wittig or its related reactions using organic phosphorus.

Process No. 1:

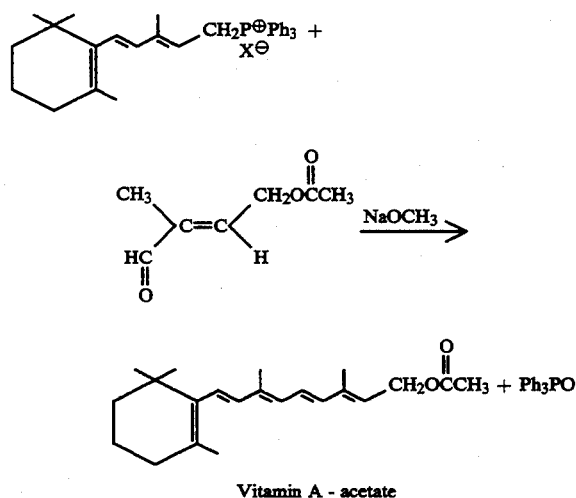

Vitamin A - acetate wherein Ph is a phenyl group, and X is halogen (Pure Appl. Chem. 43, 527 (1975)).

Process No. 2:

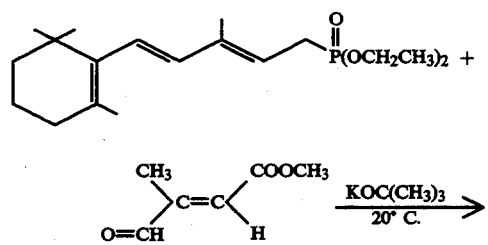

-continued
Process No. 2:

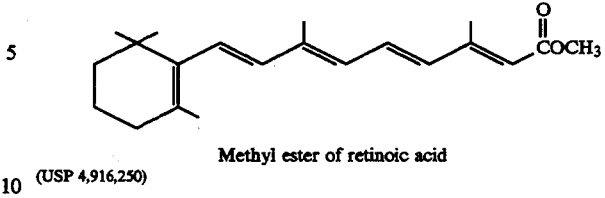

Methyl ester of retinoic acid
(USP 4,916,250)

The above processes for producing vitamin A have the following problems.

The above process No. 1, which uses the Wittig reaction, produces a large amount of cis-isomers such as 9-cis-vitamin A-acetate of the formula:

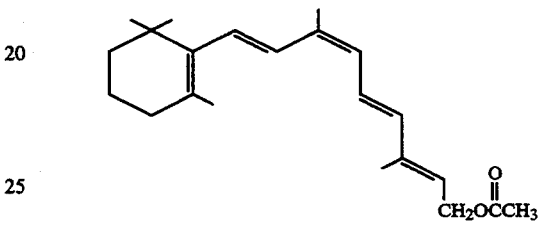

and triphenylphosphine oxide as by-products, and produces the desired product in low yield. Separation of these by-products is accompanied by complex operations and is difficult. In particular, since triphenylphosphine oxide is insoluble in water, it is very difficult to separate it from the resulting vitamin A-acetate.

The above process No. 2, which uses the Wittig-Horner reaction, cannot produce carboxylic acid esters such as an acetate or palmitate of vitamin A directly.

One reference reports on a process to obtain, such carboxylic acid esters of vitamin A, wherein an alkyl ester of retinoic acid obtained by the above process No. 2 is reduced to vitamin A, followed by acylation to give a carboxylic acid ester of vitamin A (see Angew. Chem. 72, 811 (1960)). This process is not suitable as an industrial process because the reducing agent used to reduce the alkyl ester of retinoic acid is expensive and the process involves many complicated reaction steps.

OBJECTS OF THE INVENTION

The main object of the present invention is to provide a novel process for producing vitamin A derivatives.

This object as well as other objects and advantages of the present invention will become apparent to those skilled in the art from the following description.

SUMMARY OF THE INVENTION

According to the present invention, there is provided a process for producing a vitamin A derivative, for example, a vitamin A derivative of the formula (III):

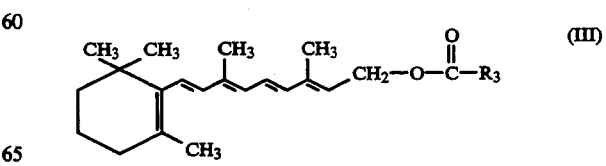

wherein $R_3$ is a hydrocarbon group, which comprises reacting a compound of the formula (I):

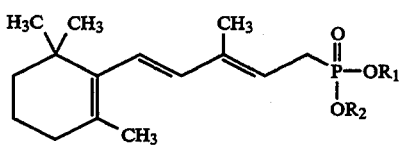

(I)

wherein $R_1$ and $R_2$ are the same or different and are each an alkyl group, with a compound of the formula (II):

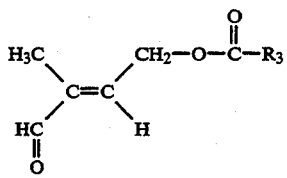

(II)

wherein $R_3$ is a hydrocarbon group, in the presence of a base.

DETAILED DESCRIPTION OF THE INVENTION

Examples of the alkyl represented by $R_1$ or $R_2$ in the above formulas include straight-chain or branched-chain alkyl groups, preferably straight-chain or branched-chain lower alkyl groups having 1 to 6 carbon atoms, for example, methyl, ethyl, n-propyl, isopropyl, n-butyl, sec-butyl, tert-butyl, pentyl, hexyl and the like. More preferred examples thereof include straight-chain or branched-chain alkyl groups having 1 to 3 carbon atoms, for example, methyl, ethyl, n-propyl and isopropyl.

Examples of the hydrocarbon group represented by $R_3$ include saturated or unsaturated hydrocarbon groups having 1 to 20 carbon atoms. Preferred examples thereof include alkyl groups, cycloalkyl groups, alkenyl groups, cycloalkenyl groups, alkynyl groups and the like. More preferred examples thereof include alkyl groups having 1 to 20 carbon atoms, for example, methyl, ethyl, propyl, butyl, pentyl, hexyl, octyl, nonyl, decyl, undecyl, dodecyl, tridecyl, tetradecyl, pentadecyl, hexadecyl, heptadecyl, octadecyl, nonadecyl, eicosyl and the like. Particularly preferred examples thereof are a methyl or pentadecyl group. When $R_3$ is a methyl group, vitamin A-acetate can be produced. When $R_3$ is a pentadecyl group, vitamin A-palmitate can be produced.

Examples of the base include inorganic bases such as alkaline metal hydrides and organic bases such as organic alkaline metal salts (e.g., alkaline metal salts with alcohols, sulfoxides, etc.) and the like. Organic bases such as organic alkaline metal salts are preferred. Examples of the alkaline metal hydride include sodium hydride, potassium hydride and the like. Examples of the organic alkaline metal salt include alcoholates (e.g., sodium t-butoxide, potassium t-butoxide, etc.), alkaline metal salts of sulfoxides (e.g., dimsylsodium, dimsylpotassium, etc.) and the like, more preferably alcoholates obtained from lower alcohols having 1 to 5 carbon atoms and alkaline metals (e.g., sodium t-butoxide, potassium t-butoxide, etc.).

The amount of the base to be used is preferably about 1 to 3 mol per mol of the compound of the formula (I) (hereinafter referred to as the compound (I)).

The amount of the compound of the formula (II)(-hereinafter referred to as the compound (II)) to be used is preferably about 1 to 2 mol per mol of the compound (I).

In a preferred process embodying the present invention, the compound (I) is reacted with the compound (II) in the presence of a base as follows.

This reaction is preferably carried out in an organic solvent. Any organic solvents can be used so long as they do not have a detrimental effect on this reaction. As the organic solvent, aprotic solvents can preferably be used. Examples of the solvent include nonpolar aprotic solvents such as hydrocarbons (e.g., hexane, cyclohexane, benzene, toluene, etc.), ethers (e.g., diethyl ether, diisopropyl ether, dimethoxyethane, tetrahydrofuran, dioxane, etc.); polar aprotic solvents such as nitriles (e.g., acetonitrile, etc.), ketones (e.g., acetone, etc.), amides (e.g., dimethylformamide, dimethylacetamide, N-methylpyrrolidone, hexamethylphosphoric triamide, etc.) and the like. Preferred examples thereof are hydrocarbons (e.g., hexane, cyclohexane, benzene, toluene, etc.), ethers (e.g., diethyl ether, diisopropyl ether, dimethoxyethane, tetrahydrofuran, dioxane, etc.) and the like. These organic solvents can be used alone or as mixtures of two or more solvents at an appropriate ratio.

This reaction proceeds more advantageously in a mixed solvent of two or more of the above organic solvents, for example, in a mixed solvent of a nonpolar aprotic solvent and a polar aprotic solvent. The nonpolar aprotic solvent preferably has a dielectric constant of 10 or less. The polar aprotic solvent is preferably selected from polar aprotic solvents having a dielectric constant from at least about 15 to at most about 60, preferably from at least 20 to at most about 50. Examples of the polar aprotic solvent include N,N-dimethylformamide, dimethylacetamide, dimethyl sulfoxide, N-methylpyrrolidone, hexamethylphosphoric triamide, acetonitrile and the like. A combination of a non-polar aprotic solvent such as toluene or diisopropyl ether and a polar aprotic solvent such as N,N-dimethylformamide is preferred. The amount of the polar aprotic solvent to be used is about 5 to 50% v/v, preferably about 10 to 25% v/v based on the total amount of the solvent.

The reaction temperature is in the region of about $-95°$ C. to about $+20°$ C., preferably about $-70°$ C. to about 0° C. In general, this reaction gives high yields at a low temperature. If necessary, the reaction may be carried out under an atmosphere of an inert gas such as helium, nitrogen, argon or the like.

The reaction time is not specifically limited and is about 5 minutes to about 5 hours, preferably about 5 minutes to about 2 hours.

The order of the addition of the compounds (I) and (II) and the base is not specifically limited. Preferably, compounds (I) and (II) and the base are dissolved in an organic solvent.

For example, the compound (I) is dissolved in an organic solvent and then the compound (II) and the base are simultaneously or separately added thereto at a low temperature. Alternatively, the base is dissolved in an organic solvent and the compounds (I) and (II) are simultaneously or separately added thereto at a low temperature. Preferably, in the process of the present invention, the compound (I) is dissolved in an organic solvent and then the compound (II) and the base are simultaneously added thereto at a low temperature.

The vitamin A derivatives produced by the process of the present invention have preferably an all-trans side chain. All of these vitamin A derivatives are sometimes referred to as the "all-trans form". The all-trans form of the vitamin A derivative is, for example, represented by the formula (III):

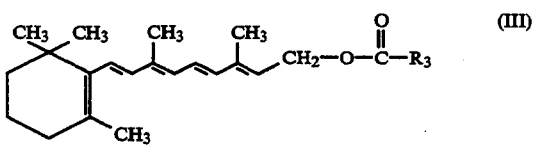

wherein $R_3$ is as defined above.

The vitamin A derivatives obtained by the process of the present invention can be isolated and purified by per se known methods such as solvent extraction, solvent conversion, redistribution, crystallization by salting out, recrystallization, chromatography or the like. For example, after completion of the reaction, water is added to the reaction mixture. If necessary, an appropriate organic solvent (e.g., diisopropyl ether, toluene, n-hexane, 1,2-dichloroethane, ethyl acetate, chloroform, etc.) is added to extract the vitamin A derivatives. Then, after washing with water, the resulting organic layer is dehydrated. The solvent is evaporated, for example, under reduced pressure at a low temperature.

The vitamin A derivatives obtained by the present process can widely be used as medicaments, feed additives, food additives and the like.

The compound of the formula (I) used as the starting material in the above process can readily be prepared according to per se known methods, for example, from β-ionone through the following three steps:

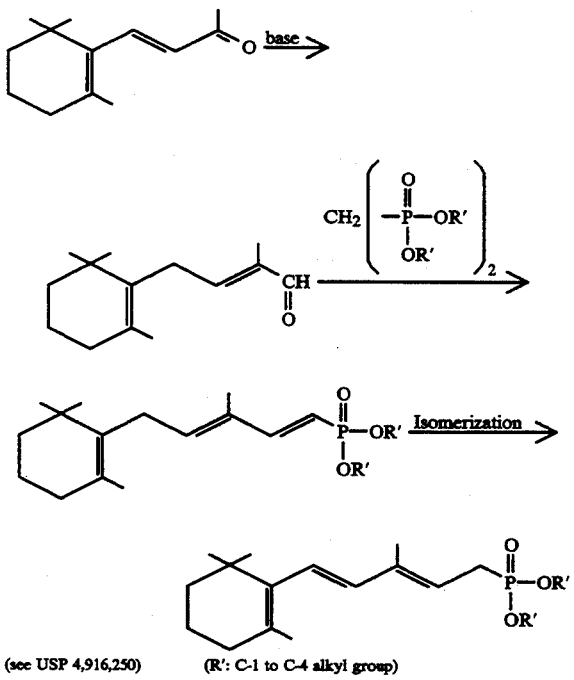

(see USP 4,916,250)   (R': C-1 to C-4 alkyl group)

The other starting material of the compound of the formula (II) can readily be prepared according to per se known methods, for example, from isoprene through the following three steps when the starting material is, for example, 4-acetoxy-2-methyl-2-buten-1-al, i.e. the compound (II) wherein $R_3$ is methyl.

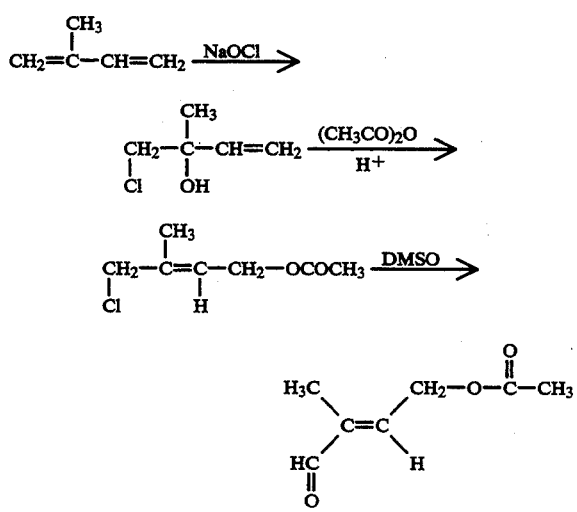

(see J. Org. Chem. 44, 10 (1979))

The compound (II) wherein $R_3$ is an unsaturated hydrocarbon group can be prepared by the above method or modifications thereof.

Alternatively, the compound (II) can also be prepared from isoprene readily according to the following scheme.

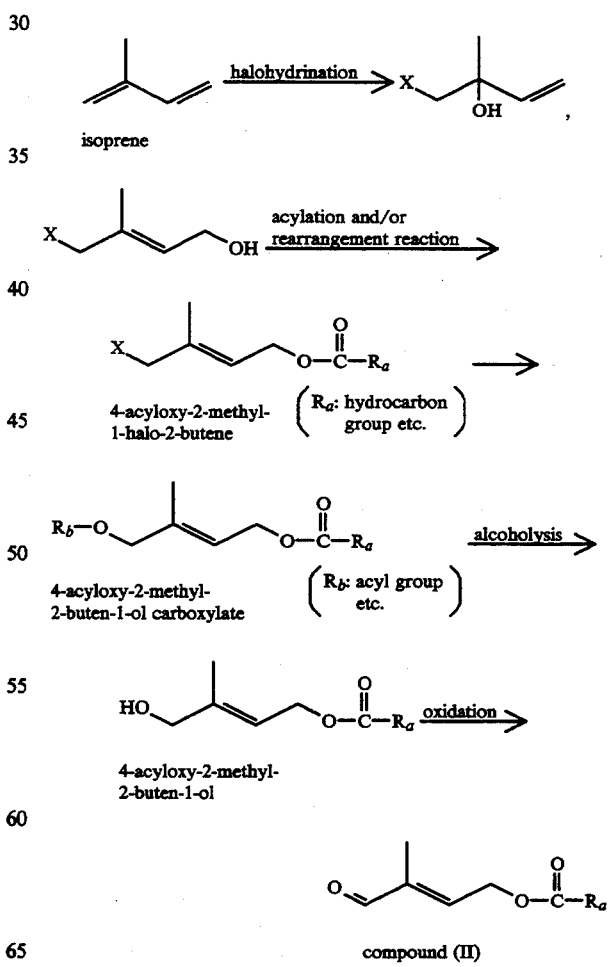

For example, isoprene is converted into a halohydrin, for example, by reacting isoprene with a hypohalogenous acid salt with an alkaline metal or alkaline earth metal (e.g., sodium hypochlorite, magnesium hypochlorite, etc.) optionally in the presence of a strong acid (e.g., sulfuric acid, etc.) as a pH adjustor. The resulting halohydrin is subjected to acylation optionally followed by a rearrangement reaction, for example, by reacting the halohydrin with an acylating agent such as an acid anhydride (e.g., acetic anhydride, propionic anhydride, etc.), acid halide (e.g., palmitoyl chloride, etc.) or the like optionally in the presence of a catalyst such as a strong acid (e.g., perchloric acid, etc.) to form 4-acyloxy-2-methyl-1-halo-2-butene. The resulting haloacyl compound is converted into an acyloxy compound, for example, by reacting the haloacyl compound with a carboxylic acid salt with a metal such as an alkaline metal (e.g., sodium, potassium, etc.) optionally in the presence of a quaternary ammonium salt such as tetra-n-alkylammonium halide (e.g., tetra-n-butylammonium bromide, etc.) to form 4-acyloxy-2-methyl-2-buten-1-ol carboxylate. The resulting acyloxy compound is subjected to alcoholysis, for example, in an alcohol (e.g., methanol, ethanol, propanol, etc.) in the presence of a catalyst such as an alkaline metal carbonate (e.g., sodium carbonate, potassium carbonate, etc.), alkaline metal bicarbonate (e.g., sodium bicarbonate, etc.) to form 4-acyloxy-2-methyl-2-buten-1-ol. The resulting alcohol is subjected to oxidation, for example, with air or oxygen gas in the presence of a catalyst such as an N-oxy radical compound (e.g., 2,2,6,6-tetramethyl-piperidine-1-oxy, etc.), cuprous chloride or the like to form 4-acyloxy-2-methyl-2-buten-1-al which is the compound (II).

Alternatively, the compound (II) can also be prepared by hydrolyzing a quaternary ammonium salt, which can be obtained from the above 4-acyloxy-2-methyl-1-halo-2-butene and hexamethylenetetramine, in water and an organic solvent homogeneously immiscible with water such as hydrocarbons (e.g., toluene, cyclohexane, etc.), halogenated hydrocarbons (e.g., 1,2-dichloroethane, etc.), ethers (e.g., diisopropyl ether, etc.), esters (e.g., ethyl acetate, etc.) or the like optionally in the presence of an acid (e.g., acetic acid, etc.) as a pH adjuster.

As described hereinabove, according to the present invention, vitamin A derivatives can readily be produced in high yield and high purity. The desired all-trans vitamin A derivatives can be produced in high yield, whereas other isomers (e.g., 9-cis isomer, 11-cis isomer, 13-cis isomer, etc.) in low yield. Therefore, the all-trans vitamin A derivatives can readily be isolated and purified by conventional methods such as recrystallization and the like.

The following examples further illustrate the present invention in detail but are not to be construed to limit the scope thereof.

EXAMPLE 1

Preparation of vitamin A acetate

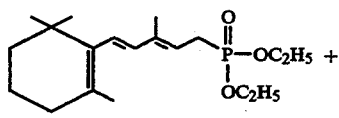

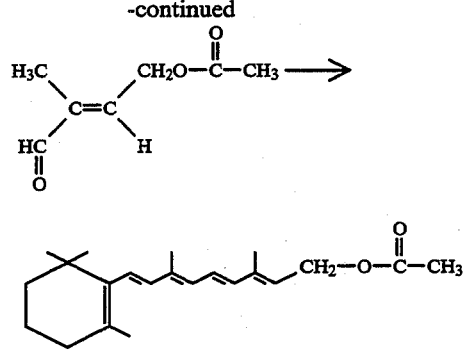

Diethyl 3-methyl-5-(2,6,6-trimethyl-1-cyclohexen-1-yl)-2,4-pentadienylphosphonate (10.0 g, purity: 93.2%, 27.4 mmol) was dissolved in toluene (40 ml), and the solution was cooled to −45° C. A solution of sodium t-butoxide powder (5 g, 52 mmol) in a mixed solution of toluene (20 ml) and dimethylformamide (20 ml) and a solution of 4-acetoxy-2-methyl-2-buten-1-al (5.0 g, 35.2mmol) in toluene (40 ml) were added dropwise simultaneously at −45° C. over about 20 minutes to the previously cooled solution. After the addition, the mixture was stirred at the same temperature for 5 minutes, followed by addition of water (20 ml) to separate the mixture into two layers. The organic layer was separated, washed with water (120 ml) twice and dried over anhydrous sodium sulfate. The sodium sulfate was filtered off. Evaporation of the solvent under reduced pressure gave a yellow solid (11.5 g).

This solid was assayed by high performance liquid chromatography under the following conditions. The yield of the resulting vitamin A acetate (all-trans form) was 92.0%. The yield of the total of the 11-cis and 13-cis isomers was 6.4% (the ratio of the resulting isomers, 11-cis:13-cis=about 2:1). The yield of the 9-cis isomer was 1.0%.

Addition of methanol (20 ml) to the solid and stirring gave crystals. After cooling to −20° C. and stirring for about 30 minutes, the resulting crystals were separated by filtration. Drying under reduced pressure gave pale yellow crystals (8.3 g). The crystals were assayed according to the first method of the vitamin A assay of the Japanese Pharmacopoeia (the 11th revision). The results showed that the purity of the vitamin A was 97.3%. The weights of vitamin A acetate and each isomer in the crystals were measured by high performance liquid chromatography under the following conditions. The results showed that the vitamin A acetate (all-trans form) was 7.76 g (yield: 86.2%), the total of the 11-cis and 13-cis isomers was 0.26 g (yield: 2.9%), and the 9-cis isomer was 0.04 g (yield: 0.4%). The mother liquor after filtration of the crystals was concentrated under reduced pressure to dryness to give a yellow solid (2.6 g). This solid was assayed by the above high performance liquid chromatography in the same manner. The results showed that the vitamin A acetate (all-trans form) was 0.53 g (yield 5.9%), the total of the 11-cis isomer and 13-cis isomer was 0.30 g (yield: 3.3%), and the 9-cis isomer was 0.03 g (yield:

Column: Nucleosil 50−5 φ 4.6×250 nm
Eluent: hexane-ether 50:1 (v/v)
Flow rate: 0.8 ml/minute
Detection: UV 310 nm

EXAMPLE 2

Preparation of vitamin A acetate

Diethyl 3-methyl-5-(2,6,6-trimethyl-1-cyclohexen-1-yl)-2,4-pentadienylphosphonate (8.0 g, purity: 93.4%, 21.95 mmol) was placed in a 300 ml flask in which the atmosphere had been replaced with nitrogen gas, dissolved in diisopropyl ether (160 ml), and the solution was cooled to −65° C. A solution of potassium t-butoxide (4.0 g, 35.65 mmol) in a mixed solution of diisopropyl ether (20 ml) and dimethylformamide (8 ml) was added dropwise to the above cooled solution over about 15 minutes while maintaining the temperature at −65° C. One to two minutes later, a solution of 4-acetoxy-2-methyl-2-buten-1-al (4.0 g, 28.14 mmol) in diisopropyl ether (20 ml) was added dropwise over about 15 minutes. After completion of the addition, the mixture was stirred at the same temperature for 5 minutes, water (200 ml) was added to the reaction mixture, and the organic layer was separated. The aqueous layer was extracted with diisopropyl ether (40 ml). The extract and the above organic layer were combined. The mixture was washed with water and dried over anhydrous sodium sulfate. The sodium sulfate was filtered off and evaporation of the solvent under reduced pressure gave a yellow oil (8.1 g).

This oil was assayed by high performance liquid chromatography according the same manner as that described in Example 1. The results showed that the yield of the resulting vitamin A acetate (all-trans form) was 83.2%. The yield of the total of the 11-cis and 13-cis isomers was 6.9%, and the yield of the 9-cis isomer was 1.3%.

EXAMPLE 3

Preparation of vitamin A acetate

Diethyl 3-methyl-5-(2,6,6-trimethyl-1-cyclohexen-1-yl)-2,4-pentadienylphosphonate (2.0 g, 5.87 mmol), dimethyl 3-methyl-5-(2,6,6-trimethyl-1-cyclohexen-1-yl)-2,4-pentadienylphosphonate (2.6 g, 8.32 mmol) and methyl ethyl 3-methyl-5-(2,6,6-trimethyl-1-cyclohexen-1-yl)-2,4-pentadienylphosphonate (4.3 g, 13.17 mmol) were dissolved in toluene (40 ml) in a 300 ml flask in which the atmosphere had been replaced with nitrogen gas. The resulting solution was cooled to −45° C. A solution of sodium t-butoxide powder (5 g, 52 mmol) in a mixed solution of toluene (20 ml) and dimethylformamide (20 ml) and a solution of 4-acetoxy-2-methyl-2-buten-1-al (5.0 g, 35.2mmol) in toluene (40 ml) were added dropwise simultaneously at −45° C. over about 25 minutes to the previously cooled solution.

Then, the mixture was treated according to the same manner as that described in Example 1 to give a solid (11.3 g). This solid was assayed according to the same manner as that described in Example 1. The results showed that the yield of the vitamin A acetate (all-trans form) was 91.4%, the yield of the total of the 11-cis and 13-cis isomers was 6.9%, and the yield of the 9-cis isomer was 1.3%.

EXAMPLE 4

Preparation of vitamin A acetate

Diethyl 3-methyl-5-(2,6,6-trimethyl-1-cyclohexen-1-yl)-2,4-pentadienylphosphonate (10 g, purity: 93.2%, 27.4 mmol) was placed in a 300 ml flask in which the atmosphere had been replaced with nitrogen gas, and dissolved in toluene (40 ml). The solution was cooled to −45° C. A solution of sodium t-butoxide (7.5 g, 78.0 mmol) in a mixed solution of toluene (75 ml) and dimethylformamide (45 ml) and a solution of 4-acetoxy-2-methyl-2-buten-1-al (5.0 g, 35.2 mmol) in toluene (40 ml) were added dropwise simultaneously over about 25 minutes to the above solution cooled to −45° C. After completion of the addition, the mixture was stirred at −45° C. for 5 minutes, and water (45 ml) was added. The organic layer was separated and washed with water (200 ml) twice. Evaporation of the solvent under reduced pressure gave a yellow solid (10.3 g).

This solid was assayed by high performance liquid chromatography according the same manner as that described in Example 1. The results showed that the yield of the vitamin A acetate (all-trans form) was 90.2%, the yield of the total of the 11-cis and 13-cis isomers was 7.0%, and the yield of the 9-cis isomer was 1.0%.

EXAMPLE 5

Preparation of vitamin A acetate

Diethyl 3-methyl-5-(2,6,6-trimethyl-1-cyclohexen-1-yl)-2,4-pentadienylphosphonate (10 g, purity: 93.2%, 27.4 mmol) was placed in a 300 ml flask in which the atmosphere had been replaced with nitrogen gas, and dissolved in diisopropyl ether (40 ml). The solution was cooled to −45° C. A solution of sodium t-butoxide (7.5 g, 78.0 mmol) in a mixed solution of diisopropyl ether (75 ml) and dimethylformamide (45 ml) and a solution of 4-acetoxy-2-methyl-2-buten-1-al (5.0 g, 35.2 mmol) in diisopropyl ether (40 ml) was added dropwise simultaneously to the above cooled solution over about 25 minutes. After completion of the addition, the mixture was stirred at −45° C. for 5 minutes, and water (45 ml) was added. The organic layer was separated and washed with water (200 ml) twice. Evaporation of the solvent under reduced pressure gave a yellow solid (10.1 g).

This solid was assayed by high performance liquid chromatography according the same manner as that described in Example 1. The results showed that the yield of the vitamin A acetate (all-trans form) was 85.0%, the total yield of the 11-cis and 13-cis isomers was 6.5%, and the yield of the 9-cis isomer was 1.3%.

EXAMPLE 6

Preparation of vitamin A acetate

Diethyl 3-methyl-5-(2,6,6-trimethyl-1-cyclohexen-1-yl)-2,4-pentadienylphosphonate (8.0 g, purity: 93.4%, 21.95 mmol) was placed in a 300 ml flask in which the atmosphere had been replaced with nitrogen gas, and dissolved in tetrahydrofuran (160 ml). The solution was cooled to −65° C. Potassium t-butoxide (4.0 g, 35.65 mmol) was dissolved in tetrahydrofuran (20 ml). 4-Acetoxy-2-methyl-2-buten-1-al (4.0 g, 28.14 mmol) was dissolved in tetrahydrofuran (20 ml). The above potassium t-butoxide solution was added dropwise to the previously cooled solution of the phosphonic acid diester over about 15 minutes while maintaining the temperature at −65° C. Dropwise addition of the above 4-acetoxy-2-methyl-2-butenal solution was started one to two minutes after beginning of the dropwise addition of the potassium t-butoxide solution, and the addition was carried out over about 15 minutes while maintaining the temperature at −65° C. After completion of the addition, the mixture was stirred at the same temperature for 5 minutes, water was added, hexane (160 ml) was added, and the resulting mixture was allowed to stand. The organic layer was separated and the aqueous layer was extracted with hexane (40 ml). This extract and the organic layer were combined, and the mixture was washed with water and dried over anhydrous sodium sulfate. The sodium sulfate was filtered off. Evaporation of the solvent under reduced pressure gave a yellow oil (8.2 g).

This oil was assayed by high performance liquid chromatography according the same manner as that described in Example 1. The results showed that the yield of the resulting vitamin A acetate (all-trans form) was 80.4%, the total yield of the 11-cis and 13-cis isomers was 5.6%, and the yield of the 9-cis isomer was 1.6%.

EXAMPLE 7

Preparation of vitamin A acetate

Diisopropyl ether (200 ml) was placed in a 300 ml flask in which the atmosphere had been replaced with nitrogen gas. Potassium t-butoxide (5.0 g, 44.56 mmol) was added, and the mixture was stirred and cooled to −40° to −50° C. To this mixture was added dropwise a solution of diethyl 3-methyl-5-(2,6,6-trimethyl-1-cyclohexen-1-yl)-2,4-pentadienylphosphonate (10.0 g, purity: 93.6%, 27.50 mmol) in diisopropyl ether (25 ml) over about 30 minutes while maintaining the temperature at −40° to −50° C. Then, to this solution was added dropwise a solution of 4-acetoxy-2-methyl-2-buten-1-al (5.0 g, 35.17 mmol) in diisopropyl ether (25 ml) over about 30 minutes while maintaining the temperature at −40° to −50° C. The mixture was stirred at the same temperature for additional 30 minutes. After completion of the reaction, water was added and the mixture was allowed to stand. The organic layer was separated and the aqueous layer was extracted with diisopropyl ether (50 ml). This extract and the organic layer were combined, washed with water and dried over anhydrous sodium sulfate. The sodium sulfate was filtered off. Evaporation of the solvent under reduced pressure gave a yellow oil (9.3 g).

This oil was assayed by high performance liquid chromatography according the same manner as that described in Example 1. The results showed that the yield of the resulting vitamin A acetate (all-trans form) was 78.4%, the total yield of the 11-cis and 13-cis isomers was 7.9%, and the yield of the 9-cis isomer was 2.9%.

EXAMPLE 8

Preparation of vitamin A acetate

60% Sodium hydride (1.18 g, 29.5 mmol) was placed in a 200 ml flask in which the atmosphere had been replaced with nitrogen gas, and washed with n-hexane (5 ml) three times. Then, dimethyl sulfoxide (15 ml) was added and the mixture was stirred at 65° C. for 45 minutes to give dimsylsodium. After cooling, tetrahydrofuran (50 ml) was added, and the mixture was cooled to −50° to −70° C. Then, diethyl 3-methyl-5-(2,6,6-trimethyl-1-cyclohexen-1-yl)-2,4-pentadienyl-phosphonate (5.0 g, purity: 93.6%, 13.75 mmol) was dissolved in tetrahydrofuran (50 ml). This solution was added dropwise to the above dimsylsodium solution over about 25 minutes while maintaining the temperature at −50° to −70° C. After stirring for 20 minutes, a solution of 4-acetoxy-2-methyl-2-buten-1-al (2.5 g, 17.59 mmol) in tetrahydrofuran (50 ml) was added dropwise to the above solution over about 20 minutes while maintaining the temperature at −50° to −70° C. The mixture was stirred at the same temperature for 20 minutes.

After completion of the reaction, the reaction mixture was added to hexane (400 ml), and water was added to separate the mixture into two layers. The organic layer was separated and the aqueous layer was extracted with hexane (200 ml). The extract and the organic layer were combined, washed with 10% (by weight) aqueous sodium chloride solution and dried over anhydrous sodium sulfate. The sodium sulfate was filtered off. Evaporation of the solvent gave a yellow oil (5.2 g). This oil was assayed by high performance liquid chromatography according to the same manner as that described in Example 1. The results showed that the yield of the resulting vitamin A acetate (all-trans form) was 70.2%, the total yield of the 11-cis and 13-cis isomers was 7.1%, the yield of the 9-cis isomer was 2.6%.

EXAMPLE 9

Preparation of vitamin A propionate

Diethyl 3-methyl-5-(2,6,6-trimethyl-1-cyclohexen-1-yl)-2,4-pentadienylphosphonate (5.0 g, purity: 94.5%, 13.88 mmol) was dissolved in toluene (50 ml) in a stream of nitrogen gas, and the solution was cooled to −60° C. A solution of sodium t-butoxide (2.5 g, 26.0 mmol) in a mixed solution of toluene (10 ml) and dimethylformamide (10 ml) and a solution of 4-propionyloxy-2-methyl-2-buten-1-al (2.8 g, 17.9mmol) in toluene (15 ml) were added dropwise simultaneously at −45° C. over about 10 minutes to the previously cooled solution. After the addition, the mixture was stirred at the same temperature for 5 minutes, followed by addition of water (20 ml). After allowing the mixture to stand, the organic layer was separated, washed with water (100 ml) twice and dried over anhydrous sodium sulfate. Evaporation of the solvent under reduced pressure gave a yellow oil (5.8 g).

The oil was assayed according to the first method of the vitamin A assay of the Japanese Pharmacopoeia (the 11th revision). The results showed that the purity of the vitamin A propionate was 63.9% (Yield: 89.5%). The contents of the vitamin A propionate (all-trans form) and each isomer in the oil were determined by high performance liquid chromatography under the conditions of Example 1. The results showed that the yield of the vitamin A propionate (all-trans form) was 82.5%, the total yield of the 11-cis and 13-cis isomers was 4.7%, and the yield of the 9-cis isomer was 1.1%.

EXAMPLE 10

Preparation of vitamin A palmitate

Diethyl 3-methyl-5-(2,6,6-trimethyl-1-cyclohexen-1-yl)-2,4-pentadienylphosphonate (5.0 g, purity: 94.5%, 13.88 mmol) was dissolved in toluene (50 ml) in a stream of nitrogen gas, and the solution was cooled to −60° C. A solution of sodium t-butoxide powder (2.5 g, 26.0 mmol) in a mixed solution of toluene (10 ml) and dimethylformamide (10 ml) and a solution of 4-palmitoyloxy-2-methyl-2-buten-1-al (6.0 g, 18.0 mmol) in toluene (20 ml) were added dropwise simultaneously at −45° C. over about 10 minutes to the previously cooled solution. After the addition, the mixture was stirred at the same temperature for 5 minutes, followed by addition of water (20 ml). After allowing the mixture to stand, the organic layer was separated, washed with water (100 ml) twice and dried over anhydrous sodium sulfate. Evaporation of the solvent under reduced pressure gave a yellow oil (7.5 g).

The oil was assayed according to the first method of the vitamin A assay of the Japanese Pharmacopoeia (the 11th revision). The results showed that the purity of the vitamin A palmitate was 80.5% (Yield: 82.9%).

A mixed solution (50 ml) of acetone and methanol (acetone:methanol=9:1 (v/v)) was added to this oil, and the mixture was cooled to −20° C. The resulting pale yellow crystals were filtered quickly and dried under reduced pressure to give oily vitamin A palmitate (5.3 g, Yield: 72.7%). The mother liquor after filtration of the crystals was assayed by high performance liquid chromatography under the conditions of Example 1. As a result, 0.43 g (Yield: 5.9%) of the vitamin A palmitate was detected.

Reference Example 1

Synthesis of isoprene chlorohydrin

95% isoprene (8.96 g, 125 mmol) and water (100 ml) were maintained at 0° C. in a 500 ml four neck flask. To this mixture were added 1N sulfuric acid (about 100 ml) and a 1 mol aqueous solution (100 ml, 1 mmol) of sodium hypochlorite while maintaining the pH of the reaction mixture at 7 to 9. During the addition, the reaction temperature was maintained at 0° C. to 5° C. The addition was completed after about 4 hours. The pH at the completion of the addition was adjusted to 6 to 7 with 1N sulfuric acid. The mixture was extracted with 1,2-dichloroethane (100 ml) three times. The extract was assayed by gas chromatography. Isoprene (2.05 g, 30.1 mmol) was recovered, and the 1,2-adduct (7.13 g, 59.1 mmol) and the 1,4-adduct (3.35 g, 27.8 mmol) were obtained. The reaction yield was 91.6%.

Reference Example 2

Synthesis of 4-acetoxy-2-methyl-1-chloro-2-butene

Acetic anhydride (9.32 g, 91.2 mmol, 1.05 equivalents) and a 60% aqueous perchloric acid solution (29.1 mg, 0.174 mmol, 0.2 mol %) were placed in a 100 ml four neck flask. Isoprene chlorohydrin (a mixture of 1,2-adduct and 1,4-adduct)(10.48 g, 86.9mmol) was added so that the reaction temperature was maintained at 15° to 20° C. After stirring for 2 hours, a 60% aqueous perchloric acid solution (145.5 mg, 0.869 mmol, 1 mol %) was added. The mixture was stirred at room temperature for additional 2 hours. After completion of the reaction, water (50 ml) and 1,2-dichloroethane (50 ml) were added, and the mixture was washed with water. Then, the 1,2-dichloroethane layer was dried over anhydrous sodium sulfate. Evaporation of the 1,2-dichloroethane followed by distillation under reduced pressure (3–5 mmHg, 60°–65° C.) gave 4-acetoxy-2-methyl-1-chloro-2-butene (12.79 g, 78.6 mmol; Yield: 90.5%).

Reference Example 3

Synthesis of 4-acetoxy-2-methyl-2-buten-1-ol formate

4-Acetoxy-2-methyl-1-chloro-2-butene (8.13 g, 50 mmol) was dissolved in dimethylformamide (25 ml) and placed in a 100 ml four neck flask. To this were added sodium formate powder (6.80 g, 100 mmol, 2 equivalents) and tetra n-butylammonium bromide (0.81 g, 2.5mmol, 5 mol %). The mixture was stirred at 40° C. for 24 hours under heating. After completion of the reaction, the reaction mixture was poured into ice-cooled water (about 30 ml)and extracted with ether (50 ml) three times. The extracted ether layer was dried over anhydrous sodium sulfate. Evaporation of the ether followed by purification by silica gel column chromatography (ethyl acetate-hexane (=1:3)) gave 4-acetoxy-2-methyl-2-buten-1-ol formate (8.18 g, 47.5 mmol; Yield: 95.0%).

$^1$H-NMR (CDCl$_3$): δ1.80 (d,3H), 2.12 (s,3H), 4.50–4.82 (m,4H), 5.72 (t,1H), 8.18 (s,1H).

Reference Example 4

Synthesis of 4-acetoxy-2-methyl-2-buten-1-ol

Sodium bicarbonate (0.40 g, 4.75 mmol, 10 mol %) was added to a solution of 4-acetoxy-2-methyl-2-buten-1-ol formate (8.18 g, 47.5 mmol) in methanol (40 ml). The mixture was stirred at room temperature for 2 hours. After completion of the reaction, most of the methanol was evaporated under reduced pressure. The resulting reaction mixture was poured into a mixture of ice-cooled water (20 ml) and ethyl acetate (100 ml). The pH of the aqueous layer was adjusted to 5 to 6 with 1N hydrochloric acid, and the ethyl acetate layer was separated. The aqueous layer was extracted with ethyl acetate (50 ml) twice. The ethyl acetate layers were combined and dried over anhydrous sodium sulfate. Evaporation of the ethyl acetate gave 4-acetoxy-2-methyl-2-buten-1-ol (6.69 g, 46.4 mmol; Yield: 97.7%) as an oil.

$^1$H-NMR (CDCl$_3$): δ; 1.82 (s,3H), 2.06 (s,3H), 2.61 (—OH,1H), 4.04 (s,2H), 4.65 (d,2H), 5.62 (t,1H).

Reference Example 5

Synthesis of 4-acetoxy-2-methyl-2-buten-1-al

To a solution of 4-acetoxy-2-methyl-2-buten-1-ol (6.69 g, 46.4 mmol) in dimethylformamide (40 ml) were added 2,2,6,6-tetramethyl-piperidine-1-oxy (0.39 g, 2.32 mmol, 5 mol %) and cuprous chloride (0.48 g, 4.64 mmol, 10 mol %). The mixture was subjected to reaction for 8 hours while bubbling oxygen at a rate of about 100 ml/min. After completion of the reaction, the reaction mixture was poured into ice-cooled water (30 ml) and extracted with ether (100 ml) three times. The extract was dried over anhydrous magnesium sulfate. Evaporation of the ether followed by purification by column chromatography (ethyl acetate-hexane (=1:3)) gave 4-acetoxy-2-methyl-2-buten-1-al (6.02 g, 42.3 mmol; Yield: 91.2%).

Reference Example 6

Synthesis of 4-acetoxy-2-methyl-2-buten-1-al

4-Acetoxy-2-methyl-1-chloro-2-butene (7.8 g) was added to a suspension of hexamethylenetetramine (6.7 g) in acetonitrile (47 ml), and the mixture was stirred at room temperature for 16 hours. The resulting crystals were separated by filtration to give crystals (12.5 g) of the quaternary ammonium salt. The salt (7.9 g) was dissolved in water (50 ml), and toluene (100 ml) was added. Acetic acid (1.5 g per addition) was added 30 minutes, 1 hour and 2 hours after the beginning of the reaction with stirring at 75° C. The reaction was stopped 6 hours after the beginning of the reaction. The toluene layer was separated and concentrated. The remaining oil was purified by silica gel column chromatography to give 4-acetoxy-2-methyl-2-buten-1-al (2.6 g, 74%).

Reference Example 7

Synthesis of 4-acetoxy-2-methyl-2-buten-1-al (a) Crude 4-acetoxy-2-methyl-1-chloro-2-butene (194 g, Purity: 83.8%, 1 mol) was added to hexamethylenetetramine (168 g, 1.2 mol)/water (1 liter), and the mixture was stirred at 35° C. for 4 hours and then separated into aqueous and organic layers. 1,2-Dichloroethane (1 liter) was added to the aqueous layer, the mixture was subjected to reaction at 72° C. for 6 hours while adjusting the pH with 1N sulfuric acid. The 1,2-dichloroethane layer was separated, 1,2-dichloroethane (1 liter) was added, and the reaction was carried out again. The 1,2-dichloroethane layers were combined and concentrated. The residue was distilled under reduced pressure to give 4-acetoxy-2-methyl-2-buten-1-al (98 g, 69%). bp.$_{0.2-0.3}$: 58°–66° C.

(b) 35% Aqueous sodium hydrogensulfite solution (9 g) and ice-cooled water (100 g) were added to the above organic layer (volume: 50 ml) containing 4-acetoxy-2-methyl-2-buten-1-al (4.3 g, determined by gas chromatography). The mixture was stirred well, and the aqueous layer was separated. To the aqueous layer was added 1,2-dichloroethane (100 ml). To this mixture was added 37% aqueous formal,dehyde solution (10 ml). The resulting mixture was stirred at 30° to 40° C. for 3 hours. The 1,2-dichloroethane layer was separated and concentrated to give 4-acetoxy-2-methyl-2-buten-1-al (3.4 g, Recovery: 79%). Total yield ((a)+(b)): 101.4 g (71.4% from 4-acetoxy-2-methyl-1-chloro-2-butene).

Reference Example 8

Synthesis of 4-propionyloxy-2-methyl-2-buten-1-al (i) Synthesis of 4-propionyloxy-2-methyl-1-chloro-2-butene A solution (151 g) containing isoprene chlorohydrin (a mixture of the 1,2-adduct and 1,4-adduct)(33% w/w, 49.8 g, 0.413 mol) in 1,2-dichloroethane was cooled to 10° to 15° C., and 60% aqueous perchloric acid solution (0.2 g, 0.0012 mol) was added. Propionic anhydride (64.5 g, 0.496 mol) was added at the same temperature, and then the mixture was stirred at room temperature for 2 hours. 60% aqueous perchloric acid solution (0.07 g, 0.0004 mol) was added, and the resulting mixture was stirred at room temperature for additional 2 hours. After completion of the reaction, the reaction mixture was poured into ice-cooled water (500 ml) and extracted with 1,2-dichloroethane (500 ml). The organic layer was washed with 5% aqueous sodium bicarbonate solution (300 ml) and then with water, and dried over anhydrous sodium sulfate. The 1,2-dichloroethane was evaporated under reduced pressure to give crude 4-propionyloxy-2-methyl-1-chloro-2-butene (64.2 g, 0.363 mol, Yield: 87.9%). The crude product thus obtained was used in the next step without further purification.

(ii) Synthesis of 4-propionyloxy-2-methyl-2-buten-1-al

The crude 4-propionyloxy-2-methyl-1-chloro-2-butene (64.0 g, 0.362 mol) obtained in the above (i) was added to a solution of hexamethylenetetramine (50.9 g, 0.363 mol) in water (345 ml), and the mixture was stirred at 35° C. for 4 hours to prepare a tetramine salt. 1,2-Dichloroethane (200 ml) was added to the reaction mixture, and compounds insoluble in water were removed by extraction. 1,2-Dichloroethane (400 ml) was further added to the aqueous layer that had been washed, and the mixture was stirred at 60° C. for 4 hours to hydrolyze the tetramine salt. After completion of the reaction, the 1,2-dichloroethane layer was separated, and 1,2-dichloroethane (250 ml) was further added to the aqueous layer for extraction. The 1,2-dichloroethane layers were combined and dried over anhydrous sodium sulfate. The 1,2-dichloroethane was evaporated under reduced pressure, and the residue was purified by silica gel column chromatography (ethyl acetate-hexane (=1:5)) to give 4-propionyloxy-2-methyl-2-buten-1-al (15.2 g, 0.0973 mol, Yield: 26.8% ).

$^1$H-NMR (CDCl$_3$): δ1.40 (t,3H), 1.79 (s,3H), 2.30 (q,2H), 4.90 (d,2H), 6.52 (t,1H), 9.42 (s,1H).

Reference Example 9

Synthesis of 4-palmitoyloxy-2-methyl-2-buten-1-al (i) Synthesis of 4-palmitoyloxy-2-methyl-1-chloro-2-butene Palmitoyl chloride (50 g, 0.182 mol) was added to a solution (80 g) containing isoprene chlorohydrin (a mixture of the 1,2-adduct and 1,4-adduct)(33% w/w, 26.4 g, 0.219 mol) in 1,2-dichloroethane under ice-cooling. After the addition, the mixture was stirred at 60° C. for about 2 hours. The reaction mixture was poured into ice-cooled water (200 ml ) and extracted with 1,2-dichloroethane (200 ml) three times. The 1,2-dichloroethane layers were combined and washed with water (300 ml), and then dried over anhydrous sodium sulfate. The 1,2-dichloroethane was evaporated under reduced pressure to give crude 4-palmitoyloxy-2-methyl-1-chloro-2-butene (60.0 g). The crude product was purified by silica gel chromatography (hexane-ethyl acetate (=99:1)) to give 4-palmitoyloxy-2-methyl-1-chloro-2-butene (27.0 g, 0.0752 mol, Yield: 34.3%).

(ii) Synthesis of 4-palmitoyloxy-2-methyl-2-buten-1-al

The crude4-palmitoyloxy-2-methyl-1-chloro-2-butene (27.0 g, 0.0752 mol) obtained in the above (i) and hexamethylenetetramine (10.5 g, 0.0750 mol) were added to acetonitrile (550 ml), and the mixture was stirred at room temperature for about 20 hours. The resulting crystals were separated by filtration and dried under reduced pressure to give a tetramine salt (26.5 g, 0.0531 mol, Yield: 70.6%). The salt (26.5 g, 0.0531 mol) was added to a mixed solution of water (50 ml), acetic acid (20 ml) and cyclohexane (250 ml), and the mixture was stirred at 60° C. for 2 hours. After completion of the reaction, water (100 ml) and 1,2-dichloroethane (200 ml) were added to the reaction mixture for extraction. The aqueous layer was further extracted with 1,2-dichloroethane (200 ml) twice. The organic layers were combined and washed with water (100 ml), and then dried over anhydrous sodium sulfate. The solvent was evaporated under reduced pressure, and the residue was purified by silica gel column chromatography (hexane) to give 4-palmitoyloxy-2-methyl-2-buten-1-al (7.3 g, 0.0216 mol, Yield: 28.7%).

$^1$H-NMR (CDCl$_3$): δ0.90 (t,3H), 1.30 (s,26H), 1.80 (s,3H), 2.38 (q,2H), 4.90 (d,2H), 6.50 (t,1H), 9.44 (s,1H).

What is claimed is:

1. A process for producing a vitamin A derivative, which comprises reacting a compound of the formula (I):

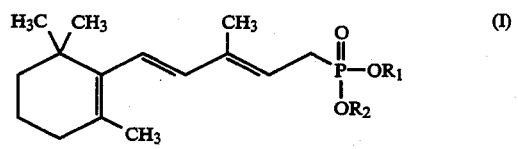

wherein R$_1$ and R$_2$ are the same or different and are each an alkyl group, with a compound of the formula (II):

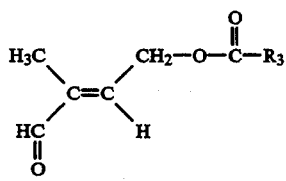

wherein $R_3$ is a hydrocarbon group, in the presence of a base.

2. A process according to claim 1, wherein $R_1$ and $R_2$ are the same or different and are each a lower alkyl group.

3. A process according to claim 1, wherein $R_3$ is an alkyl group.

4. A process according to claim 3, wherein $R_3$ is a methyl group.

5. A process according to claim 3, wherein $R_3$ is an ethyl group.

6. A process according to claim 3, wherein $R_3$ is a pentadecyl group.

7. A process according to claim 1, wherein the vitamin A derivative has an all-trans side chain.

8. A process according to claim 1, wherein the vitamin A derivative is a compound of the formula (III):

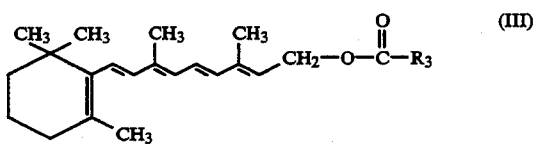

wherein $R_3$ is a hydrocarbon group.

9. A process according to claim 1, wherein the base is an organic alkaline metal salt.

10. A process according to claim 1, wherein the base is an alcoholate.

11. A process according to claim 10, wherein the alcoholate is obtained from a $C_{1-5}$ alcohol and an alkaline metal.

12. A process according to claim 1, wherein the amount of the base to be used is about 1 to 3 mol per mol of the compound of the formula (I).

13. A process according to claim 1, wherein the amount of the compound of the formula (II) is about 1 to 2 mol per mol of the compound of the formula (I).

14. A process according to claim 1, wherein the reaction is carried out in an organic solvent.

15. A process according to claim 14, wherein the organic solvent is selected from one or more of the following solvents: hydrocarbons, ethers, nitriles, ketones and amides.

16. A process according to claim 15, wherein the organic solvent is selected from hydrocarbons and ethers.

17. A process according to claim 16, wherein the organic solvent is selected from toluene and diisopropyl ether.

18. A process according to claim 1, wherein the reaction is carried out in a mixed solvent of a nonpolar aprotic solvent and a polar aprotic solvent.

19. A process according to claim 18, wherein the polar aprotic solvent has a dielectric constant of from about 20 to about 50.

20. A process according to claim 18, wherein the polar aprotic solvent is N,N-dimethylformamide or hexamethylphosphoric triamide.

21. A process according to claim 18, wherein the amount of the polar aprotic solvent is about 5 to 50% (v/v) based on the total amount of the solvent.

22. A process according to claim 1, wherein the reaction is carried out at a reaction temperature of about $-70°$ C. to $0°$ C.

* * * * *